US007705985B2

(12) United States Patent
Lucas et al.

(10) Patent No.: US 7,705,985 B2
(45) Date of Patent: Apr. 27, 2010

(54) METHOD AND APPARATUS FOR TESTING FIBRES

(75) Inventors: Stuart Lucas, Geelong East (AU); Stuart Gordon, Jan Juc (AU); Nicole Phair-Sorensen, Lara (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 672 days.

(21) Appl. No.: 10/586,842

(22) PCT Filed: Jan. 20, 2005

(86) PCT No.: PCT/AU2005/000061

§ 371 (c)(1),
(2), (4) Date: Apr. 24, 2007

(87) PCT Pub. No.: WO2005/068974

PCT Pub. Date: Jul. 28, 2005

(65) Prior Publication Data

US 2008/0151255 A1 Jun. 26, 2008

(30) Foreign Application Priority Data

Jan. 20, 2004 (AU) ................................ 2004900263

(51) Int. Cl.
*G01J 4/00* (2006.01)
(52) U.S. Cl. ......................... 356/367; 356/364; 356/370
(58) Field of Classification Search .......... 356/364–370
See application file for complete search history.

(56) References Cited

U.S. PATENT DOCUMENTS 5,500,735 A * 3/1996 Bentley et al. .............. 356/364

(Continued)

FOREIGN PATENT DOCUMENTS

| CN | 1103949 A | 6/1995 |
|----|-----------|--------|
| RU | 2 202 786 C1 | 4/2003 |
| WO | 96/10168 | 4/1996 |

OTHER PUBLICATIONS

Thibodeaux et al. "Reference method for determination of the maturity of cotton fibers." *Melliand textilberichte, International Textile Reports.* vol. 70, No. 4. 1988. pp. 243-246.

(Continued)

*Primary Examiner*—L. G Lauchman
(74) *Attorney, Agent, or Firm*—Merchant & Gould P.C.

(57) ABSTRACT

The present disclosure relates to a method for measuring the maturity or cell wall thickening of a sample of cellulosic fiber. The method at least includes exposing the sample of fiber to polarized light, capturing one or more images of the sample through crossed polar lenses and a compensator plate so that the image(s) include interference colors from the sample; and conducting computer analysis on the captured image(s) to determine the maturity or degree of cell wall thickening of the cellulosic fiber by comparing the image(s) to reference color interference data.

18 Claims, 2 Drawing Sheets

U.S. PATENT DOCUMENTS 5,598,266 A * 1/1997 Cornuejols .................. 356/367
7,289,210 B2 * 10/2007 Jang ........................... 356/364

OTHER PUBLICATIONS

Xu et al. "Evaluating Maturity of Cotton Fibers Using Image Analysis: Definition and Algorithm." *Textile Research Journal*. vol. 64. No. 6. 1994. pp. 330-335.

Han et al. "Identification and Measurement of Convolutions in Cotton Fiber Using Image Analysis." *Artificial Intelligence Review*. vol. 12. 1998. pp. 201-211.

"Standard Test Method for Maturity of Cotton Fibers (Sodium Hydroxide Swelling and Polarized Light Procedures" Designation D1442-80, ASTM Textile and Fibre Test Methods, 1980.

Zurek, et al. "A new method of determining the optical properties of cotton fibers using polarizing interference mictroscipy," Journal of Applied Polymer Science, 28:1277-1281, Jan. 1983.

Grimes. "Polarized Light Preferred for Maturity Tests." *Textile World*. Feb. 1945. pp. 161-163, 214-216.

* cited by examiner

METHOD AND APPARATUS FOR TESTING FIBRES

FIELD AND BACKGROUND OF THE INVENTION

The present invention relates to a method and apparatus for measuring the maturity or degree of cell wall thickening of a sample of naturally occurring cellulosic fibre including cotton fibre.

Cellulosic fibre such as cotton typically has a central lumen or hollow region that represents the residual protoplasm of the living fibre cell which has a cell wall. An important property affecting the quality of fibre having the structure of cellulosic fibre is the degree of thickening of the cell wall by cellulose which is sometimes referred to as fibre maturity or circularity.

Fabric manufactures and spinners regard fibre maturity as an important indicator of the suitability of the fibre for processing from both a chemical and a physical perspective.

For example, immature fibre which is fibre with little or no cell wall thickening is known for causing the following problems during processing: small entanglements called neps; irregularities in processed fibre assemblies including finished yarns; and non-uniform in dyeing of fabrics.

More generally immature fibre decreases processing efficiency and particular steps may be taken to reduce the processing difficulties depending on the maturity of the fibre.

In addition pressure to manage fibre maturity is increasingly being exerted on research agronomists and plant breeders and therefore there is a need to develop a suitable technique for testing the maturity of cellulosic crops in a farming and harvesting environment.

The measurement of fibre maturity particularly cotton fibre has been the subject of 40 years of research and is still viewed as a difficult technical problem. A technique that has in the past been used for measuring fibre maturity involves the direct measurement of the cross-sections of a fibre using a microscope to determine fibre maturity and is regarded as a benchmark for all other tests. However, this direct technique suffers from significant experimental error due to the microscope measurements involved and the limited numbers of fibres that can be practically measured. Other indirect techniques have failed to generate sufficient industry confidence because of their lack of accuracy and/or precision.

Polarized light microscopy is a technique that has long been used to investigate the crystalline structures of inorganic and inert organic materials, e.g., minerals, fibres (natural and synthetic), bone, china, chitin and some fixed sections of organisms. The technique has been used extensively in textile and industrial fibre identification and particularly of fibres that exhibit birefringent properties, i.e., fibres that behave like a uni-axial optical crystal. The optical axis in birefringent fibres is usually parallel along the fibre axis with the refractive index being dependent upon the plane of polarization of the incident light. When plane polarized light is transmitted through a birefringent object the light ray is split into two mutually perpendicular vibrating fast and slow rays, which propagate through the object at two different speeds. Upon emerging from the object a phase difference occurs between the fast and slow rays. When recombined into a single ray by passage through a second polarizor (analyzer) the rays interfere with each other, which in turn create different interference colours that highlight different crystalline characteristics.

A standard test for determining the maturity of fibres by viewing them through crossed polarizing lenses and a first-order red Selenite compensator plate is described in a text entitled "The Standard Method of Test for Maturity of Cotton Fibres (Sodium Hydroxide Swelling and Polarized Light Procedure), 354-359, Designation: D1442-00, ASTM Textile and Fibre Test Methods 2000". The compensator plate is inserted between the polarizing lenses to increase the level of retardation between the slow and fast rays and hence improve the intensity of colours produced when the rays are recombined. The compensator is also known as wavelength retardation plate or wavelength filter.

The standard test involves arranging a bundle of fibres parallel to each other with a minimum of overlapping in a solution such as water or a clear mineral oil on a glass microscope slide. A cover slide is then positioned on top of the fibres before being placed between the crossed polar lens arrangement. The interference colours appearing from the fibres are the result of the optical phenomena described above and have been classified in a text entitled "Polarized Light Preferred for Maturity Tests" *Textile World*, February 1945, by Grimes.

Table 1 below provides the accepted standard interference colours for mature and immature cotton fibres compiled by Grimes.

TABLE 1

Colours of cotton fibres under polarized light

| FIBRE CLASSIFICATION | WITHOUT SELENITE PLATE First Order | WITH SELENITE PLATE | |
|---|---|---|---|
| | | Additive Colours Second Order | Subtractive Colours First Order |
| MATURE | light yellow white | Yellow Green | Light yellow Yellow |
| IMMATURE | gray-blue gray | Blue Purple | Orange-yellow Orange |

A disadvantage of the standard test is that the operator must make an assessment of the colours of the fibres and make a subjective decision on the colour of the fibres which gives rise to large discrepancies in the results from different laboratories. Furthermore, the test is too slow to be carried out for routine testing applications in terms of both specimen preparation and test time. According to our experience, ordinarily the time period required to carry out the standard test on a sample of fibres is in excess of 30 minutes. There would also be additional time in preparing the specimen prior to testing.

It is an object of the present invention to alleviate the disadvantages of the standard test method described above while measuring the maturity or cell wall thickening of cellulosic fibres including cotton.

SUMMARY OF THE INVENTION

According to the present invention there is provided a method for measuring the maturity of a sample of cellulosic fibre, the method including the steps of:
  a) exposing the sample of fibres to polarised light;
  b) capturing one or more images of the sample through crossed polar lenses and compensator plate so that the image(s) include interference colours from the sample; and
  c) conducting computer analysis on the image(s) captured in step b) to determine the maturity of the cellulosic fibre by comparing the image(s) interference colour data to reference maturity data.

The term "interference colours" has a well-known meaning in the field of polarized light microscopy and has been used in this sense throughout the specification.

In addition, throughout this specification the term "cellulosic fibre(s)" includes but is not limited to, cotton, linen, rayon, jute and hemp.

An advantage provided by the present invention is that the colours of the fibre in the image(s) are not evaluated by an operator as is the case with prior art polarization techniques. In other words, conducting computer image analysis enables the interference colours of fibre to be analytically determined without subjective interpretation.

Another advantage provided by the present invention is that the method can be carried out in test times of less than 2 minutes whereas as noted above, conventional polarised light microscopy can take up to 30 minutes to perform per sample.

It is preferred that step c) involves determining the area of particular interference colours in the image(s).

It is preferred that the reference maturity data be in the form of reference colour interference data.

It is preferred that the area of interference colours in the image(s) be determined by analysing the areas of any one or a combination of yellow, red, green and blue in the image(s).

Surprisingly, we have found that the percent area of interference colours of the fibre relate directly to cotton fibre maturity and contrary to previous thought, maturity can be evaluated completely independently of fibre perimeter or cross-sectional area. This means that the images captured can be analysed to produce values of average fibre maturity and the distribution of fibre maturity, particularly cotton fibre maturity, on the basis of interference colours alone.

It is preferred that an algorithm is used to compare the interference colours of the image(s) captured with the reference maturity data to determine an average value and/or distribution of maturity values for the sample.

Depending on how the analysis is carried out, it is possible to determine fibre maturity on the basis of each fibre in the image(s), a segment within each image, or on the basis of all of the fibres appearing in one or many images.

In the instance when the image(s) captured in step b) is a digital image(s), or is converted into a digital image, it is preferred that the area of particular interference colours appearing in the images be determined by analysing the number of pixels in the image(s) of a particular colour.

It is preferred that step c) involves determining the total area of fibre appearing in the image(s).

It is preferred that the total area of fibre in the image(s) be determined by any one or a combination of the following:
i) the number of fibres in each image(s);
ii) the length of the fibres in the image(s);
iii) the ribbon width of the fibres in the image(s); and
iv) the number of convolutions or twists per unit length of the fibre in the image(s).

Although it is possible that the total area of fibre appearing in the image(s) can be determined by analysing the image(s) in colour, it is preferred the method involves converting the image(s) in colour into monochrome image(s) to assist determining features i) to iv) (mentioned in the preceding paragraph). In the situation when the image(s) are captured or are converted into digital image(s), suitable image analysis techniques including pixel analysis can be employed.

It is preferred that computer analysis of the image(s) in step c) can also be used for determining the degree of attack on the fibres by micro-organisms including bacteria and fungi. The degree of attack is also an important indicator for fibre that is susceptible to processing problems such as differential dye uptake, and poor spinning performance and yarn quality generally.

It is even more preferred that the degree of attack on the fibre involve determining the number and dimensions of surface fractures of the fibres.

It is also preferred that the number and dimensions of surface fractures of the fibres be determined by pixel analysis.

Although it is possible that the sample of fibre being tested by the present invention can be prepared in several different ways to facilitate their image being captured and analysed, it is preferred that the images of the fibre captured in step b) be captured while the fibre is randomly spread over a microscope slide or alike transparent support member at a density which allows unmitigated expression of the first and second order interference colours. Moreover, it is preferred that the fibre density range from 200 to 300 $\mu g/cm^2$. Unlike conventional prior art techniques, the present invention is capable of operating with fibres overlapping on the microscope slide.

It is also preferred that the images be suspended in a liquid medium on the slide.

On account that the fibre being tested is a relative small object, it is necessary to magnify the fibre in the image(s) to achieve results of acceptable accuracy. It is possible that the fibre captured in the image(s) be magnified up to 100 times or more. However, it is preferred that the image(s) capture the fibres at a magnification ranging from 1.5 to 5 times its normal size. The magnification used is a trade-off between a too higher magnification which reduces the field of the view and thus the amount of fibre in the image(s) and reducing the magnification to a point where the fibres appearing in the image(s) is too small to be analysed.

In order to reduce the impact of increasing the magnification to a point where each image captures only a segment of the fibre being tested, it is preferred that the method also includes capturing a series of images, each of a different segment of the fibre, and that an average value and/or fibre maturity distribution can be determined from the images.

In the situation where a series of image(s) are captured, it is preferred that the images capture different segments of the sample of fibre. This may be achieved using different techniques, however, the most straightforward technique would be to move the sample of fibres between each image being captured.

According to the present invention there is also provided an apparatus for measuring the maturity or cell wall thickening of a sample of cellulosic fibre, the apparatus including:
a) an optical light path having a polarised light source that can be directed through a compensator plate before being transmitted through a sample of fibre being tested and a polarising lens that is crossed to the polarized light source and through which light from the sample can pass;
b) an image capturing means for capturing one or more images of the sample in (a) so that the image(s) include interference colours of the sample; and
c) a computer capable of analysing the image(s) to determine the maturity of the fibre by comparing the image(s) interference colour data to reference maturity data.

It is preferred that the reference maturity data be in the form of colour interference data.

In the instance when the image(s) captured are not digital images, it is recommended that the image(s) can be converted into digital image(s) so that the preferred analysis technique in the form of pixel image analysis can be carried out.

It is preferred that the polarising lens be crossed at a range from 85 to 95° to the polarized light source.

It is even more preferred that the polarising lens be crossed at approximately 90° to the polarized light source.

It is preferred that the image capturing means record the image(s) digitally and that the size of each pixel be equal to or greater than 6.45 μm×6.45 μm.

It is also preferred that the computer be capable of analysing the image(s) captured in a manner described above to determine any one or a combination of the following characteristics of the fibre mentioned above:

i) the average maturity and/or a maturity distribution of the sample of fibres;
    ii) the number of fibres in each image;
    iii) the ribbon width of the fibres in the image(s); and
    iv) the number of convolutions or twists per unit length of fibre in the image(s).

It is preferred that the optical light path includes: a tungsten filament bulb or white light emitting diode; two polarising lenses that are crossed at approximately 90°; and a compensator plate for enhancing the interference colours.

It is preferred that the optical light path be incorporated in a microscope that is capable of magnifying the sample of fibres up to 100 times its actual size. However, in order to optimise the accuracy of the apparatus, it is preferred that the image(s) be captured under a magnification ranging from 1.5 to 5 times the actual size.

BRIEF DESCRIPTION OF THE DRAWINGS

A preferred embodiment of the present invention will now be described with reference to the accompanying drawings, of which.

DETAILED DESCRIPTION OF THE PREFERRED EMBODIMENT

Figure 1:
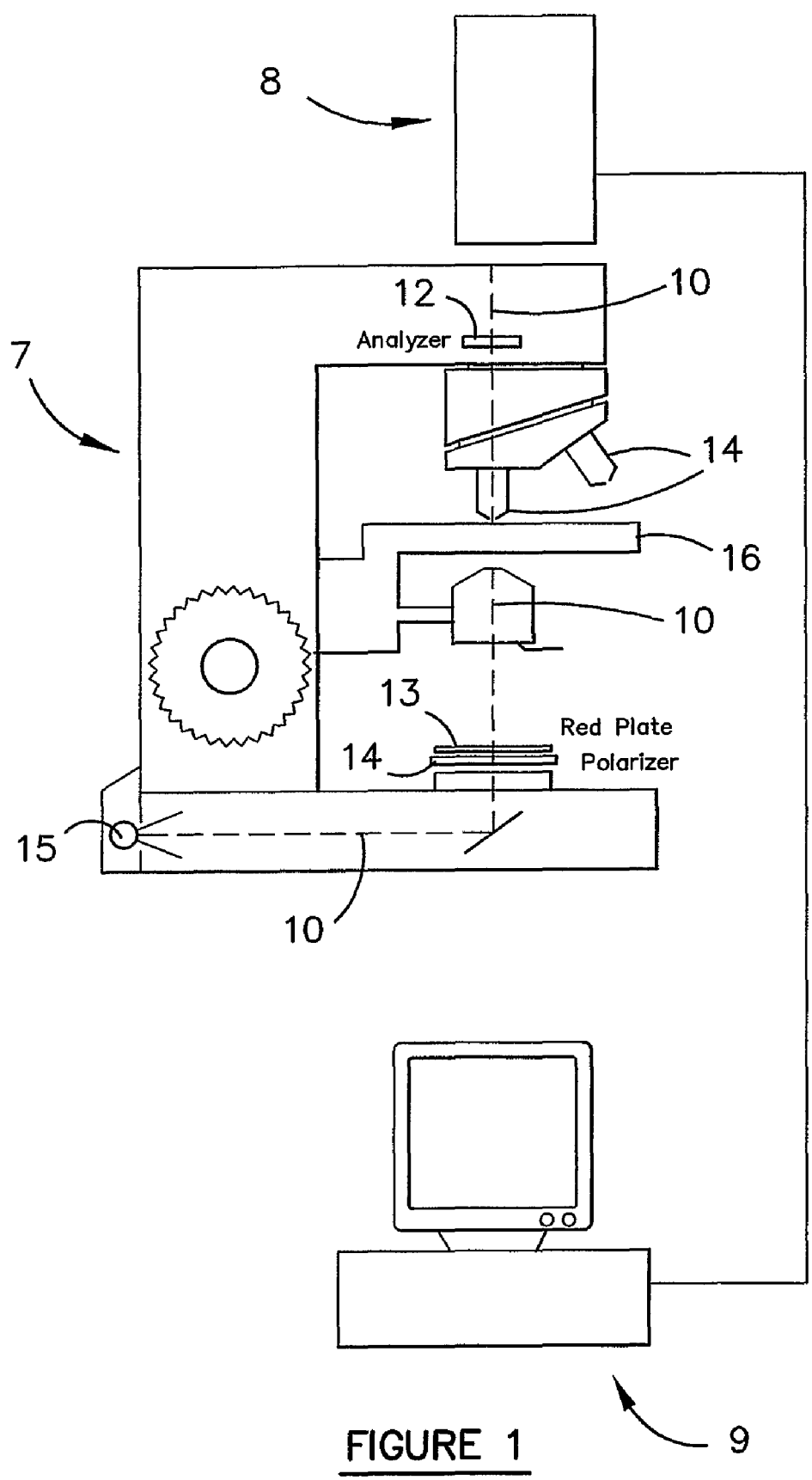
FIG. 1 is a schematic illustration of an apparatus utilised for carrying out fibre image analysis.

The preferred apparatus for conducting image analysis includes a microscope 7, a digital camera 8 for capturing images of a sample of fibres and a computer 9 for analysing the images.

The microscope is adapted for polarised light microscopy and has an optical light path 10 that includes polarising lenses 11 and 12 and a compensator plate 13 to enhance the interference colours appearing from the sample. The optical light path 10 also includes objectives lenses 14 capable of magnifying the sample of fibres up to 100 times its actual size. Preferably the microscope is operated at a magnification ranging between 1.5× and 5× so that the number of fibres in the images captured is as high as possible without compromising the accuracy of the images captured.

The compensator plate 13 is preferably made of a quartz or selenite material which retards the light by at least a quarter of a wavelength and produces the required interference colours on a red background and thus on which the properties of positive and negative bireferingence can be seen. The compensator plate is therefore often referred to a "red plate".

The optical light path 10 of the microscope 7 also includes a light source 15 that illuminates the fibre being tested. The type of light source 15 is dependent upon the interference colours to be analysed. According to the preferred apparatus a tungsten filament bulb or white light emitting diode(s) (LEDs) is used with a polarizing lens 11 and analyser 12 ordinarily crossed at 90° to each other and a first-order compensator 13 or full wavelength filter ordinarily mounted at 45° between the crossed lenses 11 and 12 to enhance the interference colours. The light source 15 and the lens 11, 12, 13, 14 defining the optical light path 10 are in some respects similar to the systems presently being used by standard polarised light microscopy techniques.

In addition, if necessary coloured LEDs can be used to augment specific areas of the image by selectively augmenting interference colours that correspond to structural features of the fibres in the images in accordance with standard practices.

The microscope 7 also includes a stage 16 upon which the fibres can be presented for analysis. Ideally the stage 16 can be moved in a plane perpendicular to the optical light path 10 by an electric stepping motor that is controlled using software integrated with the image and data analysis software of the computer 9. A microscope slide containing the sample of fibre is mounted to the stage by clamps that prevent the slide from moving so that malfocus effects are kept to a minimum.

The camera 8 for capturing the images is mounted on top of the polarized microscope 7 via a standard mount system which is not shown in the Figures. The optical light path 10 may include a condensing lens between the camera 8 and the microscope 7 to reduce the magnification so that a larger field of view can be captured. In this regard a CCD sensor large enough to capture a field of view at the preferred magnification may also be required.

The preferred camera 8 is an industrial type colour digital camera that is equipped with a 1.45 megapixel ⅔" progressive CCD sensor that uses a Bayer mosaic colour filter. The cell size of each pixel on the sensor is not less than 6.45 μm×6.45 μm with a spectral response that is relatively stronger in the red colour region than the green or blue regions. A strong yellow response is also recommended. The power and data transfer requirements should ideally be combined in the one cable via an IEEE 1394, USB1 or USB2 interface.

In use, it is preferred that the sample of fibres be prepared and presented in a way that provides consistently accurate results. Initially the fibres are guillotined into snippet lengths, e.g., 0.5 mm, 1 mm or 2 mm, and randomly spread over a large, e.g., 50 mm×70 mm, glass microscope slide using a spreading device. It is recommended that the density of fibres spread on the slide not compromise the expression of interference colours described in Table 1. A mounting medium providing good contrast is then applied in small drops over the snippets and another glass slide pressed carefully over the top as a cover slide.

The microscope slide is then positioned on the microscope stage 16 and the microscope operating nobs adjusted to the desired magnification and illumination of the sample.

One or more colour images of the sample are then captured using the digital camera 8. In order to increase the sample size of the fibres being tested and thus reduce the testing error, separate images may be taken of different segments of the sample of fibres.

The images are then sent from the camera 8 to the computer 9 which is programmed to analyse the images with reference to a preselected set of reference interference colour data for the type of fibre being tested. Specifically, analysis is carried out by the computer 9 analysing the colour of the pixels in the images which are then compared to maturity reference data to determine maturity values and maturity distributions.

Any suitable algorithm may be used by the computer 9 for determining average maturity values and distribution values.

The computer 9 may also be programmed so as to be capable of converting colour images into monochrome images whereby the computer 9 can carry out pixel analysis to determine other properties of the fibre in the image(s) such as:
- the total area of the fibres in each image;
- the number of fibres in each image;
- the length of the fibres in the image(s);
- the ribbon width of the fibres in the image(s); and
- the number of convolutions or twists per unit length of the fibre in the image(s).

In addition, if the fibre includes fractures caused by micro-organisms and/or bacteria, the computer 9 can also carry out pixel analysis to determine the number and dimensions of the fractures on the surface of the fibre and thus the level or degree of attack on the fibres.

Figure 2:
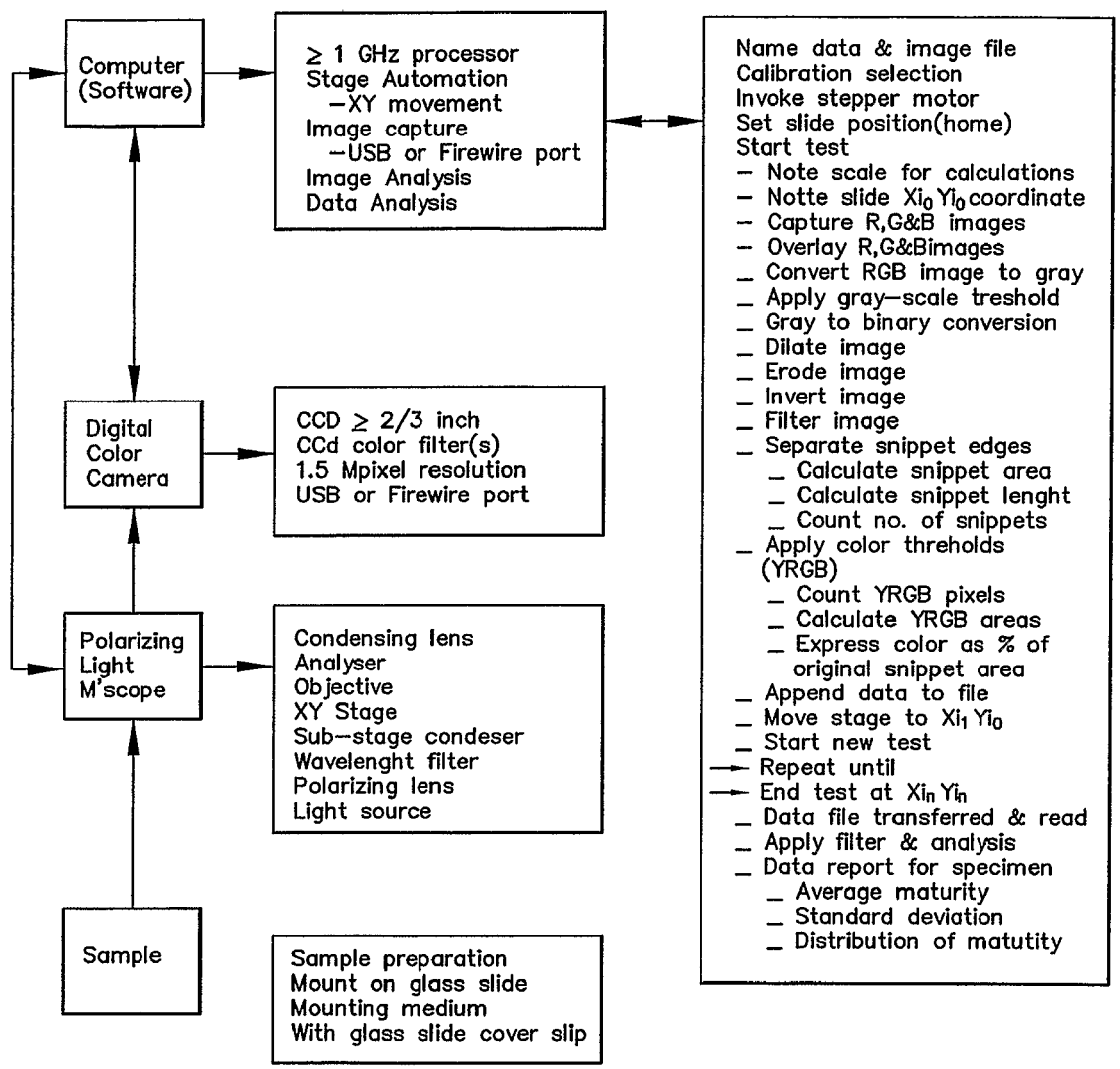
FIG. 2 is a block diagram showing the equipment items and an outline of the steps carried out in conducting fibre image analysis using the apparatus shown in FIG. 1.

The right hand column in FIG. 2 provides a detailed breakdown of the steps taken by the computer 9 during the analysis of the image(s). The information included in FIG. 2 has been included for illustration purposes only and is by no means limiting of the preferred embodiment.

The left hand column of FIG. 2 lists the physical features of the apparatus; namely a microscope having an optical path for carrying out polarizing light microscopy, a camera in the form of a digital camera, and computer software operated by the computer 9. The central provides a range of specification data and information on each component of the apparatus.

It would be appreciated by those skilled in the art that many modifications may be made to the preferred embodiment without departing from the spirit and scope of the present invention.

For example, computer analysis of the images captured may be carried out using any suitable algorithms and programs entered on the computer.

The invention claimed is:

1. A method for measuring the maturity or cell wall thickening of a sample of cellulosic fibre comprising a plurality of individual fibres, the method including the steps of:
   a) exposing the sample of fibre to polarised light;
   b) capturing one or more images of the sample through crossed polar lenses and compensator plate so that the image(s) include interference colours from the sample; and
   c) conducting computer analysis on the image(s) captured in step b) to determine the maturity of the cellulosic fibre by comparing the image(s) interference data to maturity reference data, and wherein an average value of fibre maturity and a fibre maturity distribution is determined for the sample of fibre.

2. The method according to claim 1, wherein step c) involves determining the area of particular interference colours in the image(s).

3. The method according to claim 2, wherein the area of interference colours in the image(s) is determined by analysing the areas of any one or a combination of yellow, red, green and blue in the image(s).

4. The method according to claim 2, wherein the image(s) captured are a digital image(s), or are converted into a digital image(s), and the area of particular interference colours appearing in the image(s) is determined by analysing the number of pixels in the image(s) of a particular colour.

5. The method according to claim 1, wherein conducting computer analysis involves using an algorithm to compare the interference colours of the image(s) captured with reference maturity data to determine the at least one of an average value of fibre maturity and a fibre maturity distribution for the sample.

6. The method according to claim 1, wherein step c) involves determining a total area of fibre appearing in the image(s).

7. The method according to claim 6, wherein the total area of fibre in the image(s) is determined by any one or a combination of the following:
   i) the number of fibres in the image(s);
   ii) the length of fibre in the image(s);
   iii) the ribbon width of the fibre in the image(s); and
   iv) the number of convolutions or twists per unit length of the fibre in the image(s).

8. The method according to claim 7, whereby when image(s) captured are colour, the method involves converting the image(s) in colour into monochrome image(s) in determining any one of features i) to iv).

9. The method according to claim 7, whereby when the image(s) are captured as digital image(s), or are converted into digital image(s), the method involves pixel analysis in determining any one of features i) to iv).

10. The method according to claim 1, further including determining the degree of attack on the fibre of the sample using computer analysis of the images to determine the number and dimensions of surface fractures.

11. The method according to claim 10, wherein the number and dimensions of surface fractures of the fibres is determined by pixel anaylsis.

12. The method according to claim 1, wherein the image(s) of the fibre captured in step b) is/are captured while the fibre is randomly spread over a microscope slide at a density that does not mitigate expression of the interference colours.

13. The method according to claim 12, wherein the density of fibre ranges from 200 to 300 µg/cm$^2$.

14. The method according to claim 1, wherein the image(s) capture the fibres at a magnification ranging from 1.5 to 5 times its normal size.

15. The method according to claim 1, wherein the method also includes capturing a series of images, each of a different segment of the sample fibres, and that an average value and/or fibre maturity distribution is determined from the images.

16. The method according to claim 4, wherein the size of each pixel is equal to or greater than 6.45 µm×6.45 µm.

17. A method for measuring the maturity or cell wall thickening of a sample of cellulosic fibre comprising a plurality of individual fibres, the method including the steps of:
   a) exposing the sample of fibre to polarised light;
   b) capturing a series of images of the sample of fibre through crossed polar lenses and a compensator plate so that the image(s) include interference colours; and
   c) conducting computer analysis on the image(s) captured in step b) to determine the maturity of the cellulosic fibre by comparing the image(s) interference data to maturity reference data, wherein the analysis includes determining the interference data of the images as a percentage of an area of any one or a combination of yellow, red, green, and blue interference colours in the images to a total area of fibre in the images, and comparing the percentage area to the maturity reference data to determine at least one of an average value of the fibre maturity for the fibre in the images(s) and a fibre maturity distribution for the fibre in the images.

18. A method for measuring the maturity or cell wall thickening of a sample of cellulosic fibre comprising a plurality of individual fibres, the method including the steps of:
   a) randomly distributing the sample of fibre over a transparent support member;
   b) exposing the sample of fibre on the transparent support member to polarised light;
   c) capturing a series of digital images of segments of the sample through crossed polar lenses and a compensator plate so that the images include interference colours, and wherein each image captured includes the interference colours of the respective segments of the sample of fibre; and d) conducting computer analysis on the images captured in step b) to determine the maturity of the cellulosic fibre by comparing interference data of the images to maturity reference data, wherein the analysis includes determining the total area of the fibre captured in the images as a percentage of an area of any one or a combination of yellow, red, green, and blue interference colours in the images to the total area of fibre in the images by pixel analysis, and comparing the interference data to the maturity reference data to determine at least one of an average value of the fibre maturity for the fibre in the images and a fibre maturity distribution for the fibre in the images.

* * * * *